United States Patent
Spahn

(10) Patent No.: US 7,593,555 B2
(45) Date of Patent: Sep. 22, 2009

(54) METHOD AND UNIT FOR REFINING DIGITAL X-RAY IMAGES

(75) Inventor: Martin Spahn, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/561,377

(22) PCT Filed: Jun. 16, 2004

(86) PCT No.: PCT/EP2004/006483

§ 371 (c)(1),
(2), (4) Date: Mar. 6, 2007

(87) PCT Pub. No.: WO2004/110276

PCT Pub. Date: Dec. 23, 2004

(65) Prior Publication Data

US 2007/0140542 A1    Jun. 21, 2007

(30) Foreign Application Priority Data

Jun. 17, 2003   (DE) ................................. 103 27 294

(51) Int. Cl.
   *G06K 9/00*   (2006.01)
(52) U.S. Cl. .................. 382/128; 382/100; 382/130; 382/132; 382/154; 600/437; 600/407; 378/116; 378/115; 378/165; 378/37; 378/62
(58) Field of Classification Search ................. 382/100, 382/128, 132; 378/62, 115, 116, 4, 16; 600/437
   See application file for complete search history.

(56) References Cited

U.S. PATENT DOCUMENTS

| | | | |
|---|---|---|---|
| 5,048,105 A | | 9/1991 | Adachi |
| 5,832,055 A | * | 11/1998 | Dewaele ....................... 378/62 |
| 5,889,894 A | | 3/1999 | Ito et al. |
| 6,539,103 B1 | * | 3/2003 | Panin et al. .................. 382/131 |
| 6,542,579 B1 | * | 4/2003 | Takasawa .................... 378/165 |
| 6,819,786 B2 | * | 11/2004 | Hirai .......................... 382/132 |
| 6,920,201 B2 | * | 7/2005 | Maack et al. ................ 378/116 |

(Continued)

FOREIGN PATENT DOCUMENTS

| | | |
|---|---|---|
| DE | 199 44 731 A1 | 4/2001 |
| DE | 100 52 540 A1 | 5/2002 |
| JP | 02278478 A | 11/1990 |
| JP | 09093426 A | 4/1997 |
| JP | 20011223946 A | 8/2001 |
| JP | 2001351092 A | 12/2001 |

*Primary Examiner*—Vikkram Bali
*Assistant Examiner*—Nancy Bitar

(57) ABSTRACT method for simplifying the adjustment of a digital x-ray device for the refinement of the x-ray images, and to an image refining unit for carrying out said method. According to the invention, a pre-determined modification is performed on the image data of the x-ray image by at least one image processing module according to at least one parameter: the or each parameter is supplied to the image processing module from a current set of parameters; the current set of parameters is selected from a plurality of stored standard sets of parameters; an associated model image can be displayed for each standard set of parameters using stored image data; and the standard group of parameters selected by selecting the associated model image.

7 Claims, 5 Drawing Sheets

U.S. PATENT DOCUMENTS

| | | |
|---|---|---|
| 7,031,429 B2 * | 4/2006 | Akagi ......................... 378/37 |
| 2002/0085743 A1 | 7/2002 | Kawano |
| 2002/0159567 A1 * | 10/2002 | Sako et al. .................. 378/117 |
| 2002/0169567 A1 * | 11/2002 | Tyler .......................... 702/27 |
| 2002/0183606 A1 * | 12/2002 | Boehler et al. .............. 600/407 |
| 2003/0108154 A1 * | 6/2003 | Schmitt ...................... 378/115 |
| 2004/0264626 A1 * | 12/2004 | Besson ......................... 378/4 |
| 2005/0069083 A1 * | 3/2005 | Klingenbeck-Regn ....... 378/62 |
| 2006/0188066 A1 * | 8/2006 | Spahn ......................... 378/116 |
| 2007/0071166 A1 * | 3/2007 | Spahn ......................... 378/62 |

* cited by examiner

METHOD AND UNIT FOR REFINING DIGITAL X-RAY IMAGES

CROSS REFERENCE TO RELATED APPLICATIONS

This application is the US National Stage of International Application No. PCT/EP2004/006483, filed Jun. 16, 2004 and claims the benefit thereof. The International Application claims the benefits of German application No. 10327294.1 DE filed Jun. 17, 2003, both of the applications are incorporated by reference herein in their entirety.

FIELD OF INVENTION

The invention relates to a method for refining digital x-ray images in which a predetermined modification is performed on image data by at least one image processing module, dependent on at least one parameter. The invention furthermore refers to an image refining unit to implement such a method and an x-ray apparatus incorporating the image refining unit.

BACKGROUND OF INVENTION

Digital x-ray detectors have been changing classical radiography, angiography and cardioangiography for some years. Various technologies for digital x-ray detection have in some cases been in use for a long time or are just about to become commercially available. Among these digital technologies are image intensifier camera systems based on television or CCD cameras, storage film systems with an integrated or external readout unit, selenium-based detectors with electrostatic readout, and solid-state detectors with active readout matrices with direct or indirect conversion of the x-ray radiation.

In contrast to classical radiography operating with x-ray films, in digital x-ray apparatuses the x-ray image exists in electronic form, in other words in the form of image data. This enables the x-ray image to be refined by electronic image processing before display on a screen, for example in order to make an organ to be examined or a sought pathological finding particularly well visible in the medical application. Prevalent methods of digital image processing include the per-pixel application of characteristic lines for gray-scale-dependent color or brightness modification of the x-ray image, filter operations such as the application of a low-pass, high-pass or median filter, frequency-band-dependent filtering, contrast or brightness operations (also designated as windowing), and the like.

The abundance of available setting parameters normally allows the same raw image supplied by the x-ray detector to be refined into final images that can significantly differ with regard to their optical appearance. However, the expected image appearance and the appearance that is believed to be optimal generally differ from radiologist to radiologist. This leads to individual adjustments with regard to the image refining normally having to be effected in the installation of an x-ray system, in order to adapt the final images generated by the x-ray apparatus to the taste or the precedent of the x-ray department, or even to the individual radiologist.

This adjustment process must normally be performed in close collaboration between the technicians carrying out the installation and the intended users, in other words radiologists or other application specialists, particularly as the setting of the abstract parameters presupposes detailed knowledge of the image refining technology, which cannot be assumed to be the case in respect of the application specialists who are as a rule medically trained. Considerable resource requirements in terms of personnel and time are therefore associated with installation of the x-ray apparatus. This is due particularly to different sets of image processing parameters having to be created for each organ (for example thorax, hip, abdomen, skull, extremities, etc.) to be acquired by the x-ray apparatus, each projection (lateral, aperior-posterior, oblique, etc.), and possibly different generator settings (voltage, current, filtering, dose).

A method for the selection of equipment parameters for an x-ray device, such as tube voltage and tube current, is known from US 2003/0108154 A1. For selection of the equipment parameters, a sample x-ray image preselected in accordance with a user-defined parameter model is displayed to a user, which simulates an image impression of an x-ray image such as is to be expected when setting the predefined equipment parameters on the x-ray device. When a sample image is selected by the user, the assigned equipment parameters are in so doing set on the x-ray device.

SUMMARY OF INVENTION

An object of the invention is to specify a method for refining x-ray images, in which the user-specific adjustment of the parameters used for image refinement is simplified. It is also an object of the present invention to specify an image refining unit, as well as an x-ray apparatus incorporating such an image refining unit, that allow a simplified installation.

With regard to the method, this object is achieved according to the invention by the features of the claims. With regard to the image refining unit provided for implementation of the method, the object is achieved according to the invention by the features of the claims. Accordingly, the parameter or each parameter from the current parameter set is supplied to at least one image processing module of the image refining unit, which performs a predetermined modification of the image data dependent on at least one parameter. For the purposes of making user-specific settings for image refining, a plurality of standard parameter sets is stored in a model memory, from which the current parameter set can be selected. At the same time image data is stored in an image model memory, which when used for each stored standard parameter set allows an associated model image to be displayed for selection for a user. According to the invention the selection of the current parameter set from the available standard parameter sets is then performed not directly but by the user selecting the associated model image.

The buffer memory, the model memory and the image model memory are preferably separate regions on one or more shared-use storage media, for example the working memory of a computer or a hard disk.

The method according to the invention and the associated image refining unit enable intuitive settings to be made for an x-ray apparatus even though the manner of the desired image refining is made available to the user for selection not by means of the abstract parameter sets but by means of the model images which convey to the user a concrete impression of the final result to be expected from the image refining. As a result, no detailed knowledge of the technical details concerning image refining is required for making settings for the x-ray apparatus, for example a knowledge of the effect of the individual parameters. The settings for the x-ray apparatus can therefore be performed largely independently by the medical application personnel by using the method according to the invention and in particular without support from technical personnel.

In a simple form of the method only one single standard parameter set can be selected from the available standard parameter sets, which when it is selected is taken over identically as the current parameter set. In an advantageous embodiment of the invention provision is also made whereby the user can also select a plurality of standard parameter sets simultaneously, from which the current parameter set is then created by means of interpolation. To this end, in an advantageous embodiment the image refining unit has a combination module to which the selected standard parameter sets are supplied.

The current parameter set is preferably formed from a parameter-specific linear combination of the selected standard parameter sets, whereby the individual selected standard parameter sets can be weighted as desired by the user according to his preference. In this context "parameter-specific" means that the aforementioned linear combination is formed separately for each parameter of the parameter set. If the parameter set includes a two-dimensional field or a matrix of parameters $p_{ij}$ (i,j=1, 2, 3, . . . ), then the parameter-specific linear combination of the standard parameter sets $P^{Nr.1}$ ($1=k_1$, $k_2$, . . . with k1, k2, . . . ∈ 1, 2, . . . , K) selected from the available standard parameter sets $P^{Nr.k}$ (k=1, 2, . . . , K) is represented mathematically by the equation $$p_{ij}^{akt} = \sum_l a_l \cdot p_{ij}^{Nr.l} \qquad \text{EQ. 1}$$

In EQ. 1 the symbol $p_{ij}^{Nr.1}$ stands for the parameter $p_{ij}$ which is contained in the selected standard parameter set $P^{Nr.1}$. Likewise, the symbol $p_{ij}^{akt.}$ stands for the parameter $p_{ij}$ in the current parameter set $P^{akt}$. The sum in EQ. 1 extends through all the selected standard parameter sets $P_{Nr.1}$ (1=k1, k2, . . . ). The symbol $a_1$ denotes the weighting factor of the selected standard parameter set $P^{Nr.1}$. Each weighting factor $a_1$ is a number whose value lies between 0 and 1, whereby the sum of all weighting factors $a_1$ (1=k1, k2, . . . ) yields 1.

If the parameter set contains parameters $p_{ij}(x)$ which are defined in the form of a function, then the parameter-specific linear combination is represented by the equation $$p_{ij}^{akt}(x) = \sum_l a_l \cdot p_{ij}^{Nr.l}(x). \qquad \text{EQ. 2}$$

In one variant of the method, provision is made whereby previously refined model images are stored for each standard parameter set. Each stored model image has thus already been modified compared with the underlying raw image in accordance with the associated standard parameter set. This image data can be displayed directly to the user. In this variant of the method, comparatively little data processing effort is therefore associated with the display of the model images.

In contrast, in an alternative embodiment of the method, provision is made whereby image data is stored which corresponds to a raw image acquired by the x-ray apparatus. In this situation, the model image is first created prior to display by initially feeding the stored raw image data to the image processing module or modules and modifying it in accordance with the associated standard parameter set. The advantage of this variant of the method lies in its flexibility. In particular, with this variant of the method the standard parameter sets can also be easily modified without having to exchange the stored image data.

Advantageously, the range of stored standard parameter sets made available is diversified to the effect that different standard parameter sets are stored for different parts of the body to be examined (for example, thorax, hip, abdomen, skull, extremities, etc.), each projection (for example, lateral, aperior-posterior) and possibly different generator settings which differ for example in respect of voltage, current, filtering or dose.

The image refining unit described above is incorporated according to the invention in an x-ray apparatus having the features described in the claims. In particular, this x-ray apparatus has an x-ray source to generate x-ray radiation and a digital x-ray detector to acquire an x-ray image. The x-ray image is supplied according to the invention in the form of image data to the image refining unit which is part of a control and evaluation system which is preferably computer-aided.

The advantage of this x-ray apparatus consists particularly in the fact that the adjustment process required for the image processing parameters during the course of its installation is simplified and can be performed largely independently by the application personnel.

BRIEF DESCRIPTION OF THE DRAWINGS

Embodiments of the invention will be described in the following with reference to the drawings. In the drawings.

DETAILED DESCRIPTION OF INVENTION

Figure 1:
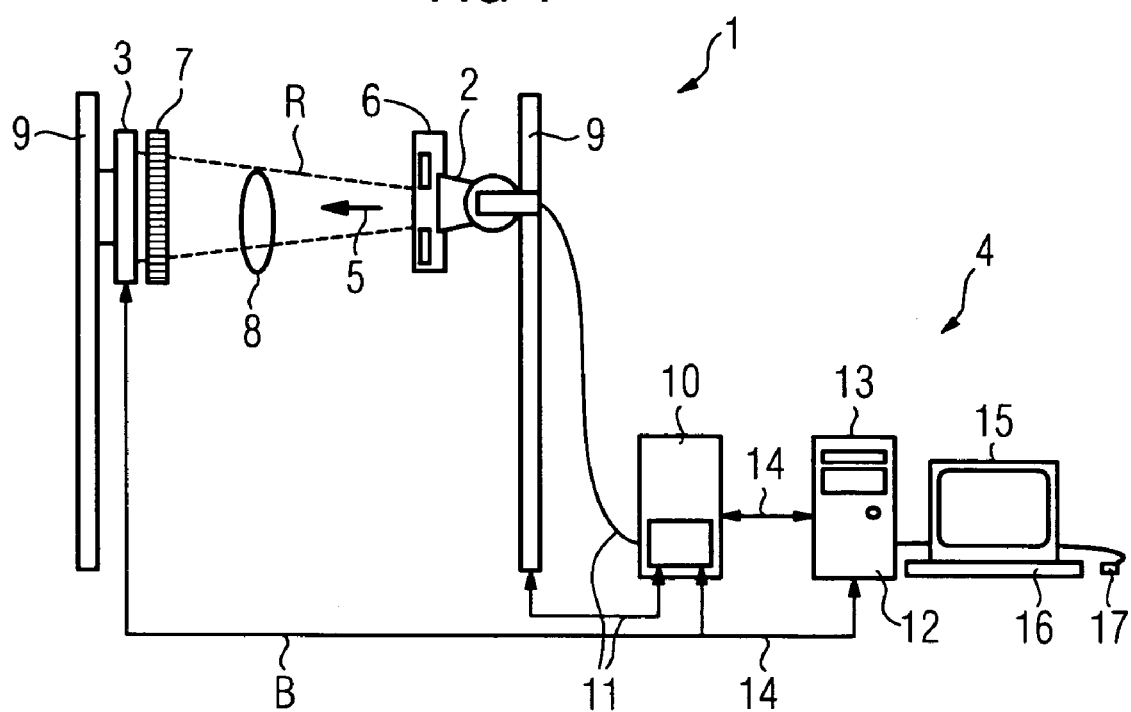
FIG. 1 shows a schematic illustration of an x-ray apparatus with an x-ray source, a digital x-ray detector and a control and evaluation system with an image refining unit.

Parts and variables corresponding to one another are always provided with the same reference characters in the FIGS.

The x-ray apparatus 1 shown schematically in FIG. 1 has an x-ray source 2, a digital x-ray detector 3 and a control and evaluation system 4. A diaphragm 6 and a scattered-ray grid 7 are interposed between the x-ray source 2 and the x-ray detector 3 in the direction of radiation 5. In this situation, the diaphragm 6 serves to allow a selected portion of a desired size to be cut from the x-ray radiation R generated by the x-ray source 2, said selected portion passing through a person to be examined 8 or an object to be examined and the scattered-ray grid 7 onto the x-ray detector 3. In this situation, the scattered-ray grid 7 serves to suppress lateral scattered radiation that would adulterate the x-ray image acquired by the x-ray detector 3.

The x-ray source 2 and the x-ray detector 3 are attached to a stand 9 or above and below an examination table, such that they can be adjusted.

The control and evaluation system 4 includes a control unit 10 to control the x-ray source 2 and/or the x-ray detector 3, and to generate a supply voltage for the x-ray source 2. The control unit 10 is connected with the x-ray source 2 by way of data and supply lines 11. The control and evaluation system 4 furthermore includes an image refining unit 12. The image refining unit 12 is preferably a component of a data processing system 13 which, in addition to image processing software, includes operating software for the x-ray apparatus 1. The data processing system 13 is connected with the control unit 10 and the x-ray detector 3 by way of data and system bus lines 14. For entering and displaying data, the data processing system 13 is furthermore connected with peripheral devices, in particular a monitor 15, a keyboard 16 and a mouse 17.

Figure 2:
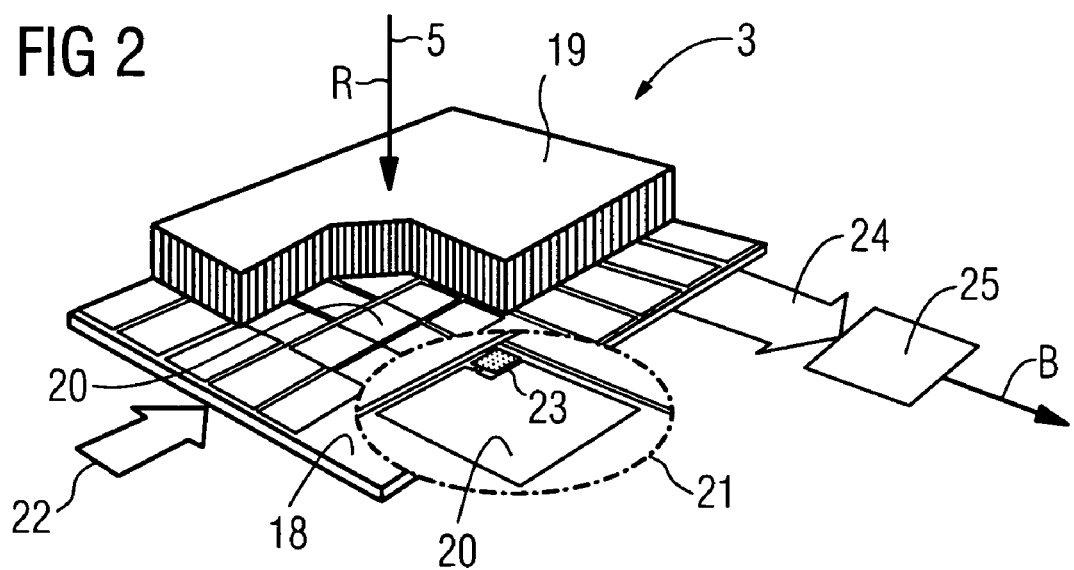
FIG. 2 shows a schematic illustration of the x-ray detector in a perspective and partially cut away view.

The x-ray detector 3 shown in detail in FIG. 2 is of a type known as a solid-state detector. It has a planar active readout matrix 18 made of amorphous silicon (aSi) which is coated with an x-ray converter layer 19, for example cesium iodide (CsI). In this x-ray converter layer 19, the x-ray radiation R striking in the radiation direction 5 is converted into visible light, which is transduced into electrical charge in photodiodes 20 of the readout matrix 18. This electrical charge is in turn stored spatially resolved in the readout matrix 18. The stored charge can, as indicated in the section 21 shown enlarged in FIG. 2, be read out in the direction of the arrow 24 to electronics 25, indicated only schematically, by means of electronic activation 22 of a circuit element 23 associated with each photodiode 20. The electronics 25 generates digital image data B by means of amplification and analog-to-digital conversion of the read-out charge. The image data B is transmitted to the image refining unit 12 by way of the data and system bus line 14.

Figure 3:
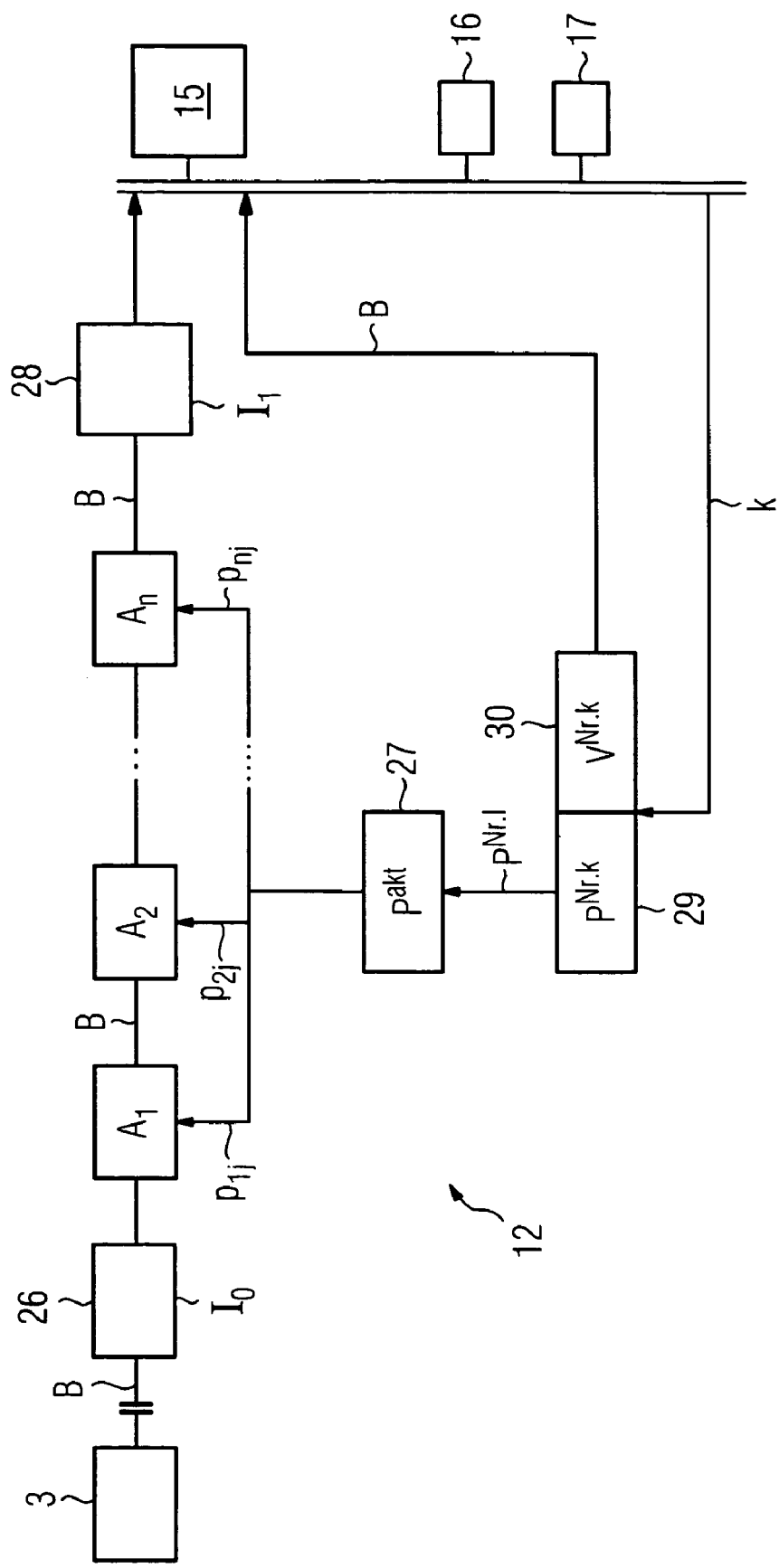
FIG. 3 shows the image refining unit of the apparatus according to FIG. 1 in a simplified block diagram.

The image refining unit 12 is preferably implemented in the form of a software module in the data processing system 13. A simplified block diagram of the image refining unit 12 is shown in FIG. 3. According to this, the image data B produced by the x-ray detector 3 is first supplied to an input memory 26. The input memory 26 thus contains image data B representing a "raw image" $I_0$, in other words an non-refined x-ray image. Starting from the input memory 26, the image data B is successively supplied to a number of image processing modules $A_i$ (i=1, 2, . . . , n), each of which modifies the image data B in a predetermined manner. The image processing modules $A_i$ are, for example, an image definition module, filter modules (in particular low-pass filter, high-pass filter, median filter and combinations thereof), contrast and brightness modules, frequency-dependent filter modules, or modules for characteristic line-dependent modification of the image data. Each image processing module $A_i$ is controlled by one or more parameters $p_{ij}$ (i=1, 2, . . . , n; j=1, 2, . . . , $m_i$).

In the example, it is assumed that the first image processing module $A_1$ is a module for contour emphasis ("edge enhancement"). For example, the size of the filter kernel, the degree of mixing of a high-pass image, a signal level above—or below—which the filter acts or is suppressed, or the like can be used as parameters $p_{11}$, $p_{12}$, $p_{13}$, . . . associated with this module $A_1$.

Each parameter $p_{ij}$ can also contain an individual number or a characteristic line $p_{ij}(x)$, in other words a functional dependency.

The entirety of all parameters $p_{ij}$ is designated as parameter set P. The parameter set P can be represented, for example, as a two-dimensional field or matrix of the individual parameters $p_{ij}$, or be handled in data form.

In the operation of the x-ray apparatus 1, a current parameter set $P^{akt}$ is made available to the image processing module $A_i$. This current parameter set $P^{akt}$ is preferably stored temporarily in a buffer memory 27.

The parameter values contained in the current parameter set $P^{akt}$ form the basic setting for the image refining unit 12, so to speak. The image processing modules $A_i$ modify the image data B in accordance with the parameters $p_{ij}$ stored in the current parameter set $P^{akt}$. The image data B modified in this way, which henceforth contains a "final image" $I_1$, is placed in an output memory 28. The final image $I_1$ can then be displayed for example on the monitor 15.

If the final image $I_1$ does not meet the expectations of the user, the user can change the current parameter set $P^{akt}$ and thereby change the settings for image refining. For this purpose, the image refining unit 12 is provided with a model memory 29 in which a total number of K (K=2, 3, 4, . . . ) standard parameter sets $P^{Nr.k}$ are stored. The letter k (k=1, 2, 3, . . . ) here stands for a count index which serves to identify the individual standard parameter set $P^{Nr.1}$, $P^{Nr.2}$, . . . .

With regard to the simplified variant of the image refining unit 12 shown in FIG. 3 the user can, as described in detail below, select from the available standard parameter sets $P^{Nr.k}$ an individual standard parameter set $P^{Nr.1}$ (1∈1, 2, . . . , K) which is assigned to the current parameter set $P^{akt}$ whose parameter settings are thus transferred to the current parameter set $P^{akt}$.

In order to offer the user an intuitive selection of the desired standard parameter set $P^{Nr.1}$, the image refining unit 12 furthermore contains an image model memory 30. A model image $V^{Nr.k}$ which can be displayed on the monitor 15 is stored in this image model memory 30 in the form of image data B for each standard parameter set $P^{Nr.k}$. Each model image $V^{Nr.k}$ corresponds to a final image, in other words to a raw image modified in accordance with the parameter values of the associated standard parameter set $P^{Nr.k}$. The model image $V^{Nr.k}$ thus conveys to the user a visual impression as to what final result is to be expected with regard to image refining when a particular standard parameter set $P^{Nr.k}$ is selected. The user then selects the desired standard parameter set $P^{Nr.k}$ indirectly by selecting the associated model image $V^{Nr.k}$. This can be done for example by the user using the mouse 17 to click on the model image $V^{Nr.k}$ displayed on the monitor 15 or using the keyboard 16 to enter the corresponding count index k or other form of identifier for the model image $V^{Nr.k}$. A major advantage of the method consists particularly in the fact that the user is no longer forced to come in contact with the abstract parameters $p_{ij}$ for image refining. This makes handling of the x-ray apparatus 1 easier, particularly for those users who are not familiar with the technical details of image refining.

By preference, different standard parameter sets $P^{Nr.k}$ are made available for different body parts or organs to be examined, different acquisition projections and different settings for the x-ray generator. For example, the first five standard parameter sets $P^{Nr.1}$ to $P^{Nr.5}$ contain different image refining variants which are intended for image acquisition of the ribcage (thorax) using a frontal acquisition projection (aperiorposterior) and a particular generator setting. The following five standard parameter sets $P^{Nr.6}$ to $P^{Nr.10}$ could for example provide different parameter settings for thorax image acquisitions using a lateral acquisition projection, etc. It can be easily seen that the number of standard parameter sets $P^{Nr.k}$ to be provided for all standard situations can be extremely large. In order to make the choice from this large number of standard parameter sets $P^{Nr.k}$ easier for the user, it is expedient to provide a menu prompting facility (not described in more detail) which guides the user step by step to his objective. For example, the user is initially prompted to specify the organ to be examined, the desired acquisition projection and the generator setting. Only those model images $V^{Nr.k}$ which correspond to the preselected combination of organ, projection and generator setting are subsequently displayed to the user for selection of the parameter set to be used.

Figure 4:
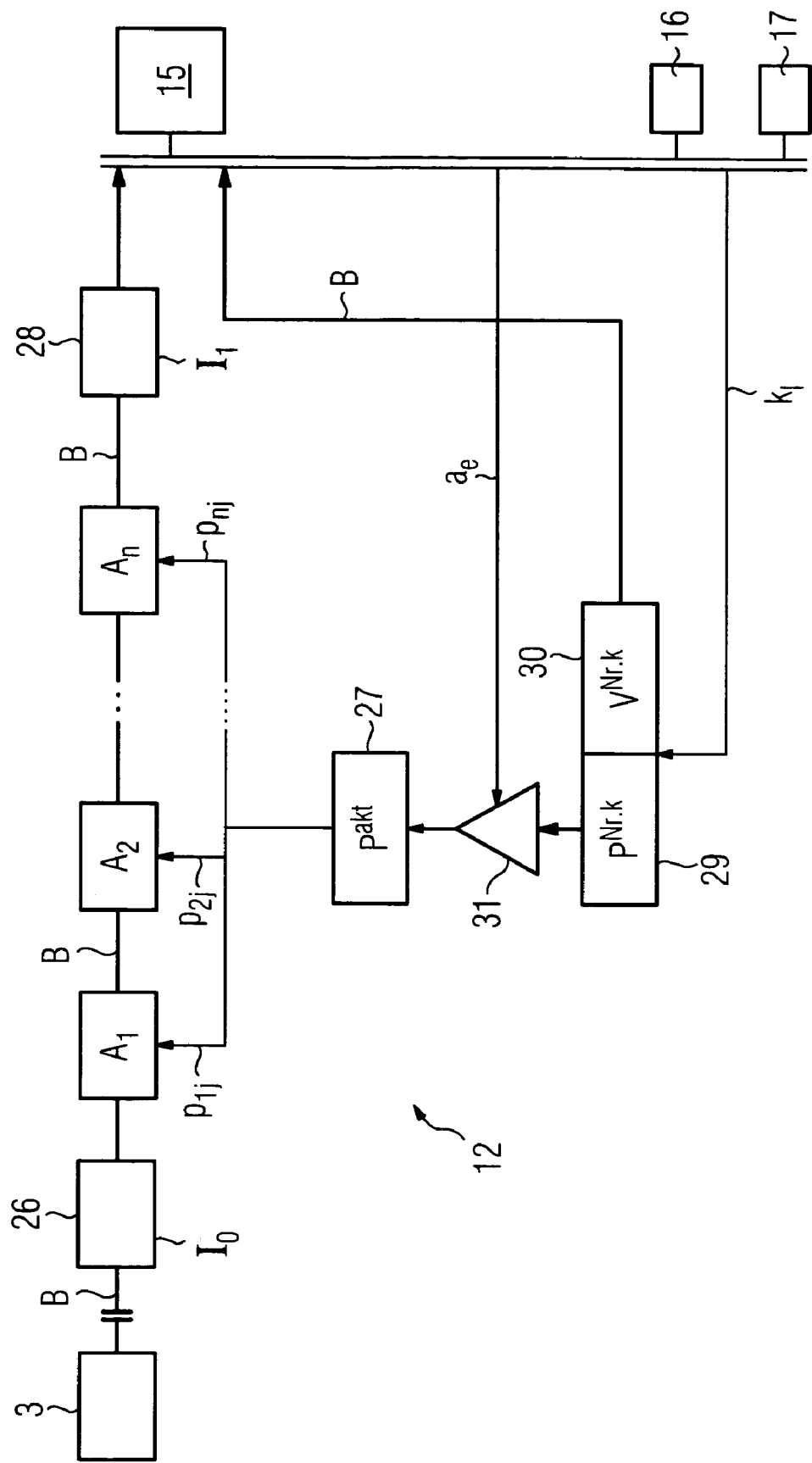
FIG. 4 shows an expanded embodiment of the image refining unit in a representation according to FIG. 3.

FIG. 4 shows an expanded embodiment of the image refining unit 12. In this embodiment the user can make not only a simple selection of an individual standard parameter set $P^{Nr.1}$ as the current parameter set $P^{akt}$. Rather, he can also simultaneously select a plurality of standard parameter sets $P^{Nr.1}$ ($1=k_1, k_2, \ldots$ with $k_1, k_2 \in 1, 2, \ldots K$), from which the current parameter set P is created by interpolation in a combination module 31. In this situation, the user makes a weighted selection, in other words he is prompted to specify the relative contribution of each selected standard parameter set $P^{Nr.1}$ by giving an associated weighting factor $a_l$.

The user can for example select the first and third parameter sets $P^{Nr.1}$ and $P^{Nr.3}$ in a weighting ratio of 40:60. In the nomenclature used here this corresponds to $k_1=1$, $k_2=3$ and also $a_1=0.4$ and $a_3=0.6$. Using the selected standard parameter sets $P^{Nr.1}$ and weighting factors $a_l$, the combination module 31 creates the current parameter set $P^{akt}$ by forming the parameter-specific linear combination according to EQ. 1 and 2. The result is stored in the buffer memory 27 as a new current parameter set $P^{akt}$.

Figure 5:
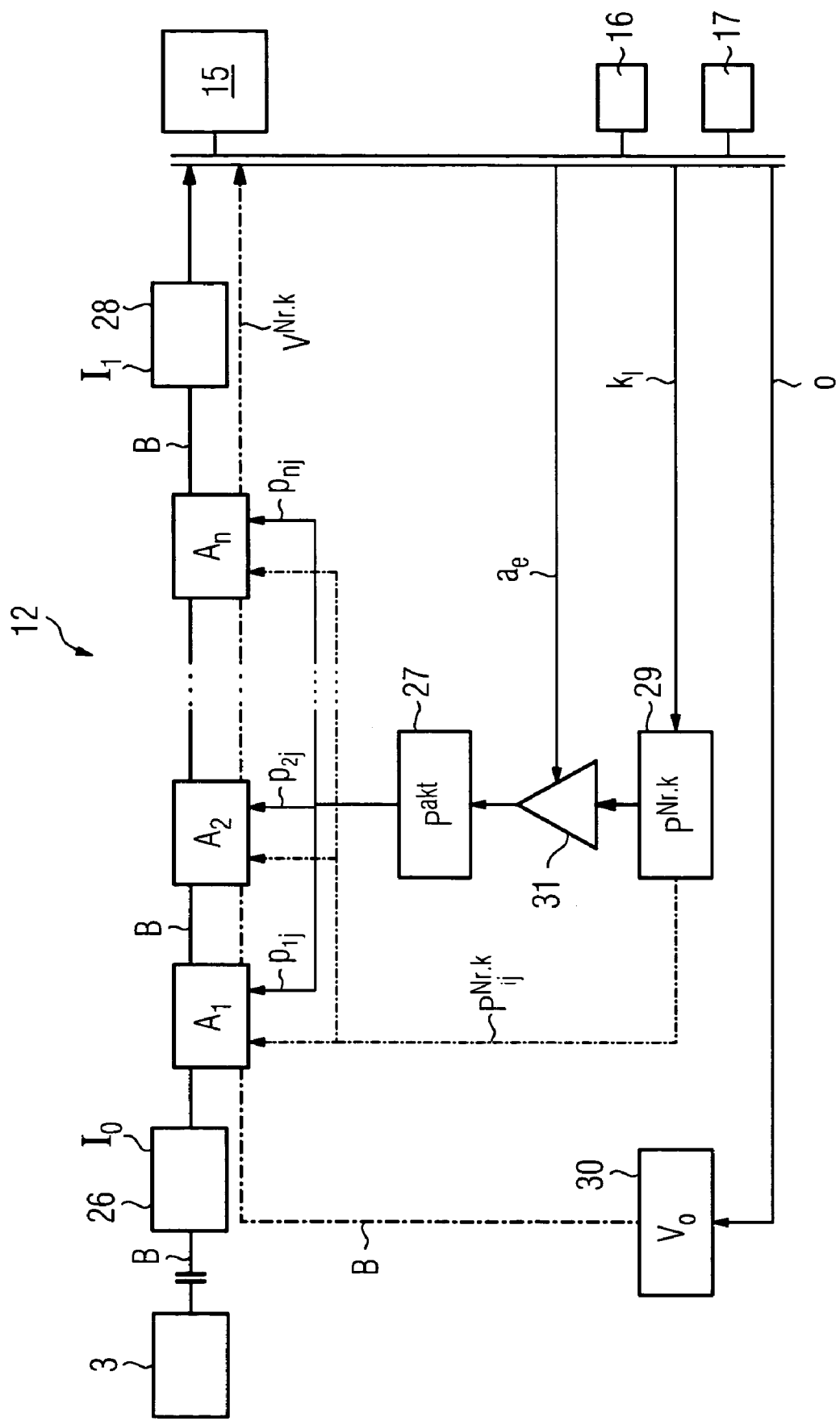
FIG. 5 shows an alternative embodiment of the image refining unit in a representation according to FIG. 3.

With regard to a variant of the image refining unit 12 shown in FIG. 5, it is raw image models $V_o$ ($o=1, 2, 3, \ldots$) and not final images that are stored in the image model memory 30. The image model memory 30 advantageously includes raw images of the different organs to be examined in different acquisition projections and with different generator settings. In this situation, the index o serves to identify the individual raw image models $V_o$.

In order to display a model image $V^{Nr.k}$ assigned to a predetermined standard parameter set $P^{Nr.k}$, a raw image model $V_o$ is initially selected (in a manner which is not described in further detail) which matches the standard parameter set $P^{Nr.k}$ in respect of the combination of organ, acquisition projection and generator setting. This raw image model $V_o$ is supplied to the processing modules $A_i$ and modified as predetermined by the parameters $p_{ij}^{Nr.k}$ contained in the standard parameter set $P^{Nr.k}$. The model image $V^{Nr.k}$ produced in this manner from the raw image model $V_o$ is displayed on the monitor 15.

Figure 6:
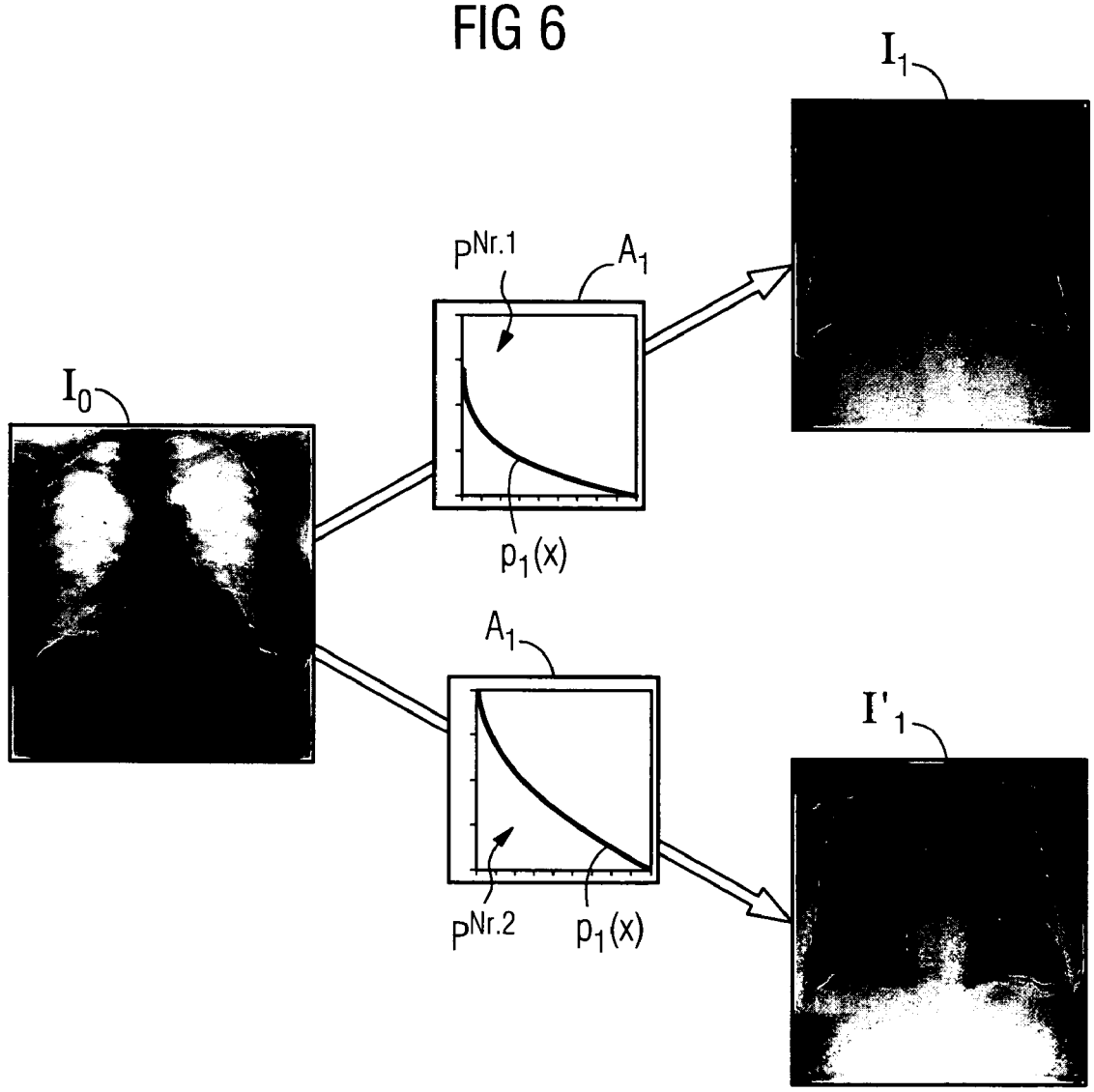
FIG. 6 shows in an exemplary comparison a raw image acquired by the x-ray detector as well as two final images modified using different standard parameter sets.

To provide a clear illustration, an image of a thorax acquired by the x-ray detector 3 is compared in FIG. 6 by way of example in the form of the raw image $I_0$ and also in two different final images $I_1$ and $I_1'$. For image refining, a processing module $A_1$ was used here in each case that effects a grey-scale shift of the individual pixels according to a characteristic line, in other words a functional parameter $p_1(x)$. The differing optical impression of the final images $I_1$ and $I_1'$ stems from the fact that the parameter $p_1(x)$ for creating the final images $I_1$ and $I_1'$ was taken from two different standard parameter sets $P^{Nr.1}$ and $P^{Nr.2}$.

The invention claimed is:

1. A method for image refining of digital x-ray images, comprising:
    using a processor to do the following steps;
    providing an image processing module;
    supplying to the image processing module a parameter from a current parameter set;
    displaying an associated model image for a standard parameter set by using a stored image data;
    selecting at least some standard parameter sets from a plurality of available standard parameter sets; and
    forming a current parameter set from the selected standard parameter sets,
    wherein when a parameter set comprises a two-dimensional matrix of parameters $p_{ij}$ ($i,j=1, 2, 3, \ldots$), then a current parameter set $P^{akt}$ is formed of a linear combination of selected standard parameter sets $P^{Nr.1}$ ($1=k_1, k_2, \ldots$ with $k_1, k_2, \ldots \in 1, 2, \ldots, K$) from the plurality of available standard parameter sets $P^{Nr.k}$ ($k=1, 2, \ldots, K$), wherein said linear combination is defined by the following equation $$p_{ij}^{akt} = \sum_l a_l \cdot p_{ij}^{Nr.l},$$

wherein $p_{ij}^{Nr.1}$ represents a parameter $p_{ij}$ in a selected standard parameter set $P^{Nr.1}$, wherein $p_{ij}^{akt}$ represents a parameter $p_{ij}$ in a current parameter set $P^{akt}$, wherein a summation defined by said equation extends through each of the selected standard parameter sets $P_{Nr.1}$ ($1=\mathbf{k1}, \mathbf{k2}, \ldots$), where $a_1$ represents a weighting factor of the selected standard parameter set $P^{Nr.1}$, wherein each weighting factor $a_l$ is a number whose value ranges from a value of zero to a value of one, and wherein a sum of all weighting factors $a_l$ ($1=\mathbf{k1}, \mathbf{k2}, \ldots$) yields a value of 1.

2. The method according to claim 1, further comprising storing different parameter sets for different body organs to be examined.

3. The method according to claim 1, further comprising storing different parameter sets for different acquisition projections.

4. The method according to claim 1, further comprising storing different parameter sets for different generator settings.

5. An image refining system to modify an image data from an x-ray apparatus, comprising:
    a memory;
    a plurality of standard parameter sets stored in the memory;
    at least one current parameter sets selected from the plurality of standard parameter sets;
    an image data stored in the memory;
    a module controlled by at least one parameter from the plurality of standard parameter sets;
    an associated model image displayed for each of the plurality of standard parameter sets; and
    a combination module configured to calculate a current parameter set from a combination of the selected parameter sets, wherein when a parameter set comprises a two-dimensional matrix of parameters $p_{ij}$ ($i,j=1, 2, 3, \ldots$), a current parameter set $P^{akt}$ is formed of a linear combination of selected standard parameter sets $P^{Nr.1}$ ($1=k_1, k_2, \ldots$ with $k_1, k_2, \ldots \in 1, 2, \ldots, K$) from the plurality of standard parameter sets $p^{Nr.k}$ ($k=1, 2, \ldots, K$), wherein said linear combination is defined by the following equation $$p_{ij}^{akt} = \sum_l a_l \cdot p_{ij}^{Nr.l},$$

wherein $p_{ij}^{Nr.1}$ represents a parameter $p_{ij}$ in a selected standard parameter set $P^{Nr.1}$, wherein $p_{ij}^{akt}$ represents a parameter $p_{ij}$ in a current parameter set $P^{akt}$, wherein a summation defined by said equation extends through each of the selected standard parameter sets $P_{Nr.1}$ ($1=\mathbf{k1}, \mathbf{k2}, \ldots$), where $a_1$ represents a weighting factor of the selected standard parameter set $P^{Nr.1}$, wherein each weighting factor $a_l$ is a number whose value ranges from a value of zero to a value of one, and wherein the sum of all weighting factors $a_l$ ($1=\mathbf{k1}, \mathbf{k2}, \ldots$) yields a value of 1.

6. The method according to claim 1, wherein when a parameter set comprises parameters $p_{ij}(x)$, where (x) represents a functional relationship for said parameters, then the linear combination is defined by the following equation $$p_{ij}^{akt}(x) = \sum_{l} a_l \cdot p_{ij}^{Nr.l}(x).$$

7. The image refining system of claim 5, wherein when a parameter set comprises parameters $p_{ij}(x)$, where (x) represents a functional relationship for said parameters, then the linear combination is defined by the following equation $$p_{ij}^{akt}(x) = \sum_{l} a_l \cdot p_{ij}^{Nr.l}(x).$$

* * * * *